(12) United States Patent
    Sakamoto

(10) Patent No.:     US 10,531,853 B2
(45) Date of Patent:     *Jan. 14, 2020

(54) MEDICAL IMAGING APPARATUS PROGRAM INSTALLABLE IN MEDICAL IMAGING APPARATUS AND MEDICAL IMAGING METHOD

(71) Applicant: CANON KABUSHIKI KAISHA, Tokyo (JP)

(72) Inventor: Tsuyoshi Sakamoto, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/057,063

(22) Filed: Aug. 7, 2018

(65) Prior Publication Data

US 2018/0338737 A1   Nov. 29, 2018

Related U.S. Application Data

(63) Continuation of application No. 14/877,789, filed on Oct. 7, 2015, now Pat. No. 10,070,837.

(30) Foreign Application Priority Data

Oct. 10, 2014  (JP) ................................ 2014-209259
Jun. 30, 2015  (JP) ................................ 2015-131597

(51) Int. Cl.
    *G06K 9/00*     (2006.01)
    *A61B 6/00*     (2006.01)
    (Continued)

(52) U.S. Cl.
    CPC .............. *A61B 6/504* (2013.01); *A61B 6/032* (2013.01); *A61B 6/463* (2013.01); *A61B 6/481* (2013.01);
    (Continued)

(58) Field of Classification Search
    CPC ......... A61B 6/032; A61B 6/481; A61B 6/504; A61B 5/055; A61B 6/463; A61B 6/5217;
    (Continued)

(56) References Cited

U.S. PATENT DOCUMENTS 5,375,603 A * 12/1994 Feiler ...................... A61B 5/01
                                                                  128/898
8,684,932 B2 * 4/2014 Kataguchi ................ A61B 8/06
                                                                  600/441
(Continued)

*Primary Examiner* — Tom Y Lu
(74) *Attorney, Agent, or Firm* — Canon USA, Inc., IP Division

(57) ABSTRACT

A medical imaging apparatus includes a cardiac lumen region identifying unit, a myocardium identifying unit, and a generating unit. The cardiac lumen region identifying unit is configured to identify a cardiac lumen region from a medical image including a heart region. The myocardium identifying unit is configured to identify a face of a myocardium region obtained by extending a face of the cardiac lumen region, identified by the cardiac lumen region identifying unit, by a certain distance toward a myocardium side. The generating unit is configured to generate a color-coded image in which the face of the myocardium region, identified by the myocardium identifying unit, is colored in colors according to signal values of the medical image corresponding to positions on the face of the myocardium region.

12 Claims, 16 Drawing Sheets

(51) Int. Cl.
*G06K 9/46* (2006.01)
*G06K 9/62* (2006.01)
*G06T 11/60* (2006.01)
*G06K 9/52* (2006.01)
*A61B 6/03* (2006.01)
*G06T 7/11* (2017.01)
*G06T 7/66* (2017.01)
*G06T 7/187* (2017.01)
*A61B 5/055* (2006.01)

(52) U.S. Cl.
CPC .......... *A61B 6/5217* (2013.01); *G06K 9/4652* (2013.01); *G06K 9/52* (2013.01); *G06K 9/6215* (2013.01); *G06T 7/11* (2017.01); *G06T 7/187* (2017.01); *G06T 7/66* (2017.01); *G06T 11/60* (2013.01); *A61B 5/055* (2013.01); *G06K 2009/4666* (2013.01); *G06K 2209/051* (2013.01); *G06T 2207/10081* (2013.01); *G06T 2207/30048* (2013.01); *G06T 2207/30172* (2013.01)

(58) Field of Classification Search
CPC ......... G06K 2009/4666; G06K 9/4652; G06K 9/52; G06K 9/6215; G06K 2209/051; G06T 11/60; G06T 2207/30048; G06T 2207/10072; G06T 2207/10081; G06T 2207/30172; G06T 7/0012; G06T 7/0042; G06T 7/11; G06T 7/187; G06T 7/408; G06T 7/60; G06T 7/66
See application file for complete search history.

(56) References Cited

U.S. PATENT DOCUMENTS

| | | | |
|---|---|---|---|
| 10,070,837 B2* | 9/2018 | Sakamoto | A61B 6/463 |
| 10,186,056 B2* | 1/2019 | Senzig | G06T 11/008 |
| 2009/0232369 A1* | 9/2009 | Senegas | G06T 7/0012 |
| | | | 382/128 |
| 2010/0204579 A1* | 8/2010 | Yoshida | A61B 8/0833 |
| | | | 600/443 |

* cited by examiner

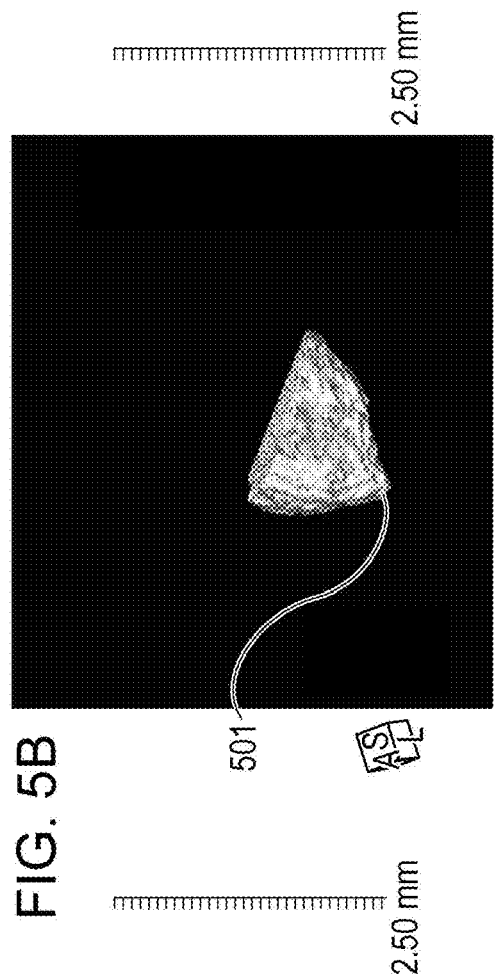
FIG. 5A
FIG. 5B
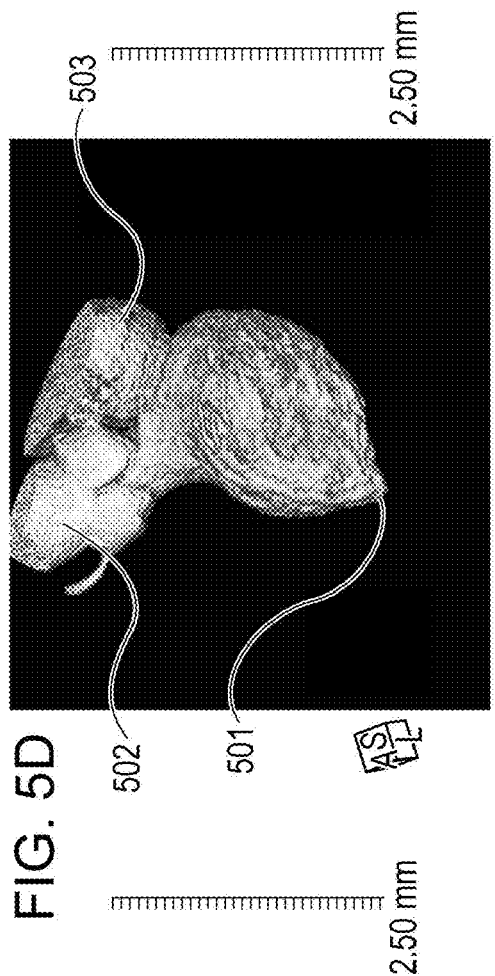
FIG. 5C
FIG. 5D

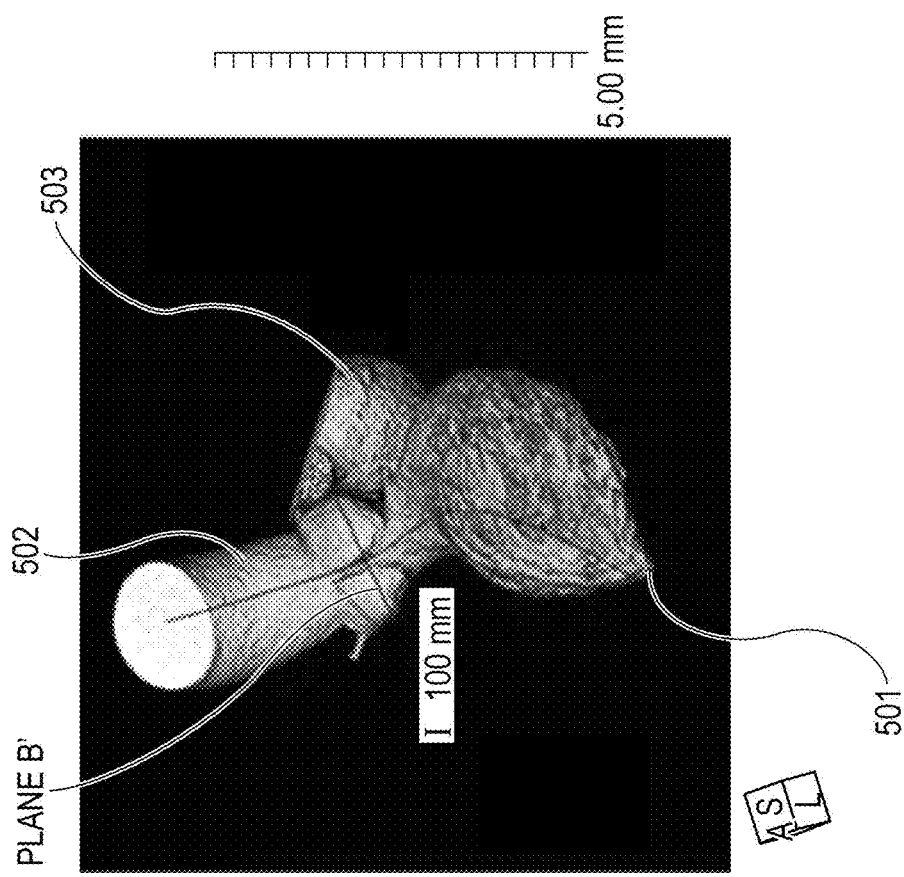
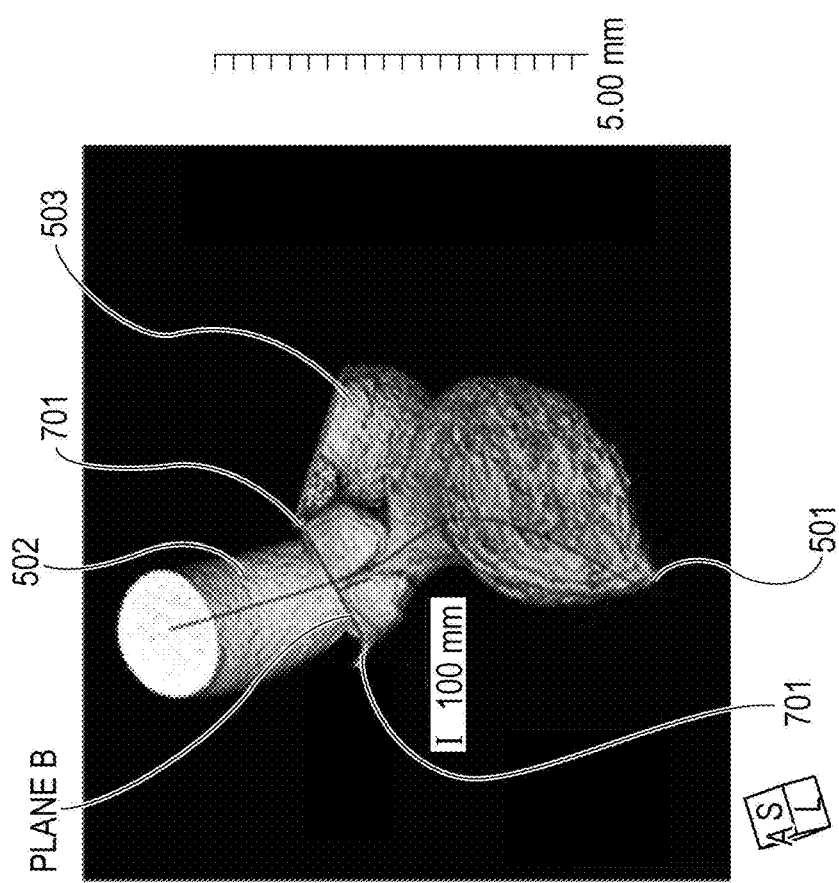

501

MEDICAL IMAGING APPARATUS, PROGRAM INSTALLABLE IN MEDICAL IMAGING APPARATUS AND MEDICAL IMAGING METHOD

CROSS REFERENCE TO RELATED APPLICATIONS

This application is a continuation, and claims the benefit, of U.S. patent application Ser. No. 14/877,789 filed Oct. 7, 2015 (now U.S. Pat. No. 10,070,837), which claims the benefit of Japanese Patent Application No. 2014-209259 filed Oct. 10, 2014 and Japanese Patent Application No. 2015-131597 Jun. 30, 2015. Each of U.S. patent application Ser. No. 14/877,789 and Japanese Patent Application numbers 2014-209259 and 2015-131597 is hereby incorporated by reference herein in its entirety.

BACKGROUND OF THE INVENTION

Field of the Invention

The present disclosure relates to a medical imaging apparatus, a program installable in a medical imaging apparatus, and a medical imaging method.

Description of the Related Art

Ischemic heart disease (IHD), which is caused by blocking the blood flow to myocardium due to obstruction or narrowing of coronary arteries, generally occurs in endocardium and progresses toward epicardium. When the disease reaches epicardium, it may be difficult to cure the disease. It is thus significantly necessary to detect the disease in an early stage. To this end, techniques for detecting narrowing of coronary arteries in an early stage by using various medical image diagnostic apparatuses have been sought in recent years.

Japanese Patent Laid-Open No. 2013-10005 discloses a medical imaging apparatus capable of detecting the presence of a narrowing of coronary arteries by obtaining a blood flow rate or the gradient of a blood flow rate in each region of coronary arteries, from a plurality of items of volume data captured at different times, which are obtained by capturing, by an X-ray computed tomographic (CT) scanner, images of the heart of a patient (subject being tested) into which a radiocontrast agent has been injected, and by generating an image that represents the form of the coronary arteries colored in accordance with the level of the blood flow rate or the gradient of the blood flow rate.

However, the medical imaging technique disclosed in Japanese Patent Laid-Open No. 2013-10005 requires to obtain a plurality of items of volume data captured at different times by the CT scanner. Not only the amount of captured data becomes vast, but also the amount of the patient's exposure to radiation becomes great. It is thus hard to say that this is a simple image generating technique.

Research on diagnosis of ischemia in recent years has found that a mechanical stress on myocardium causes an ischemic state to appear in systole. This shows the possibility that using a medical image captured in such systole can contribute to early detection of ischemic heart disease.

SUMMARY OF THE INVENTION

A medical imaging apparatus according to an embodiment of the present invention includes a cardiac lumen region identifying unit, a myocardium identifying unit, and a generating unit. The cardiac lumen region identifying unit is configured to identify a cardiac lumen region from a medical image including a heart region. The myocardium identifying unit is configured to identify a face of a myocardium region obtained by extending a face of the cardiac lumen region, identified by the cardiac lumen region identifying unit, by a certain distance toward a myocardium side. The generating unit is configured to generate a color-coded image in which the face of the myocardium region, identified by the myocardium identifying unit, is colored in colors according to signal values of the medical image corresponding to positions on the face of the myocardium region.

Further features of the present invention will become apparent from the following description of exemplary embodiments with reference to the attached drawings.

BRIEF DESCRIPTION OF THE DRAWINGS

FIGS. 5A to 5D are diagrams describing how a cardiac lumen region is extracted using a region growing method, starting from a cardiac apex side of the central line.

FIGS. 7A and 7B are diagrams describing a process of excluding an unnecessary region.

DESCRIPTION OF THE EMBODIMENTS

Hereinafter, the following technique will be described in detail. This technique generates an image to be provided for diagnosis of narrowing of coronary arteries by using one item of volume data (a plurality of items of slice image data) captured by a CT scanner in systole of a patient into which a radiocontrast agent has been injected.

A CT image captured by the CT scanner used in embodiments is an image including a heart region, which is captured while a patient (subject being tested), into which a radiocontrast agent has been injected via intravenous drip or blood vessel injection, lies on a bed. Since a portion with a radiocontrast agent absorbs more X-rays, a high CT value is obtained from this portion. By capturing a CT image in the above conditions, a CT image in which a cardiac lumen region where blood is flowing has high CT values is captured.

Figure 1:
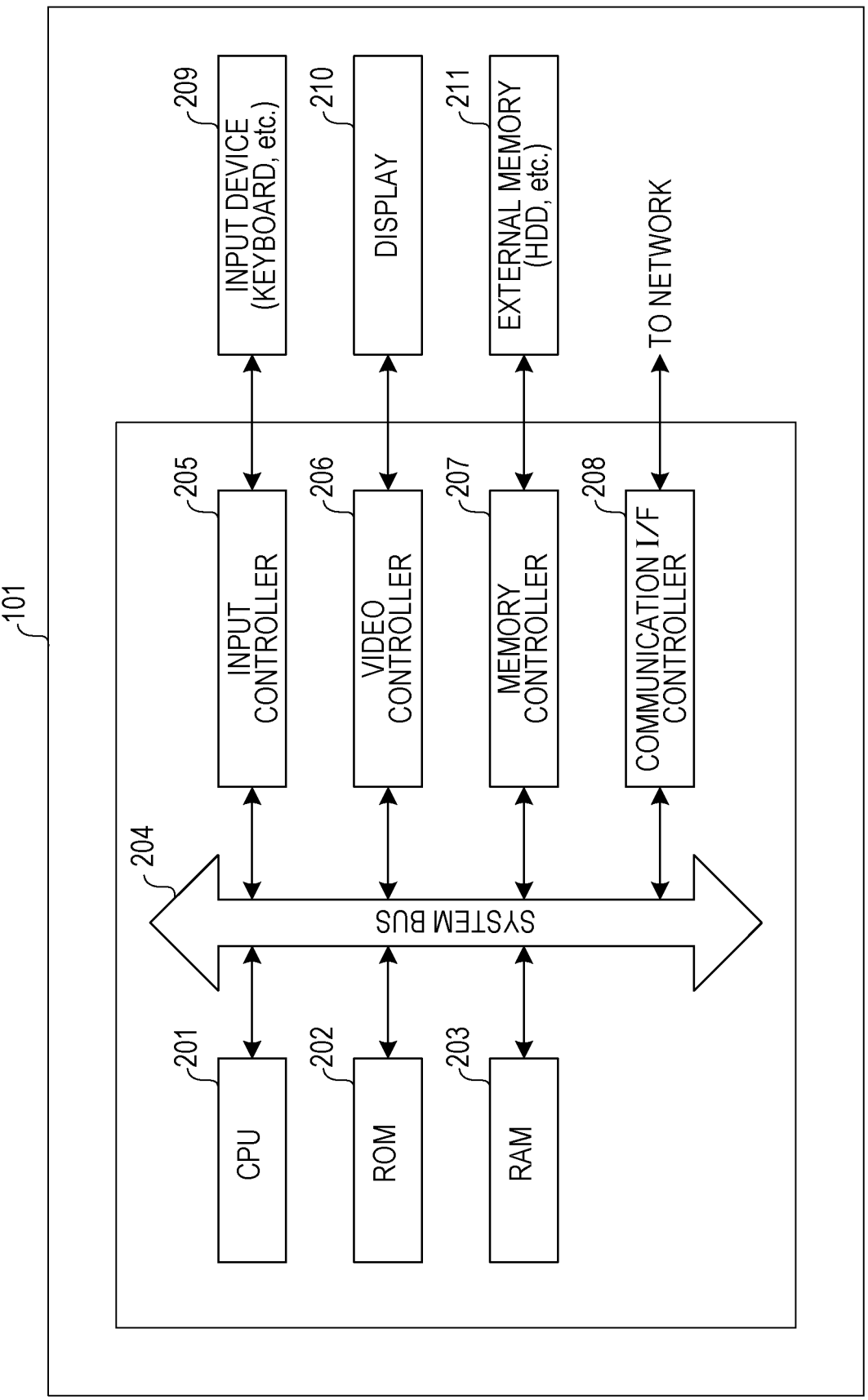
FIG. 1 is a diagram illustrating an example of the hardware configuration of a medical imaging apparatus.

FIG. 1 is a diagram illustrating an example of the hardware configuration of a medical imaging apparatus 101 according to the embodiments. The medical imaging apparatus 101 according to the embodiments is configured to obtain (load) volume data (a plurality of medical images) captured by a medical image diagnostic apparatus such as a CT scanner and stored in a storage device, and to perform image processing.

A central processing unit (CPU) 201 integrally controls devices and controllers connected to a system bus 204.

A read-only memory (ROM) 202 or an external memory 211 (storage unit) stores the Basic Input/Output System (BIOS) and an operating system program (hereinafter referred to as an OS), which are control programs for the CPU 201, and various programs, which will be described later, necessary for implementing functions executed by the medical imaging apparatus 101. A random-access memory (RAM) 203 functions as a main memory, a work area, or the like for the CPU 201.

The CPU 201 is configured to load a program necessary in executing processing to the RAM 203, and to execute the program, thereby implementing various operations.

An input controller (input C) 205 controls an input from an input device 209 such as a keyboard, a pointing device such as a mouse (not illustrated), or the like.

A video controller (VC) 206 controls display on a display device such as a display 210. It is assumed that the type of display device is a cathode-ray tube (CRT) or a liquid crystal display (LCD), but the display device is not limited to these types.

A memory controller (MC) 207 controls access to the external memory 211 such as a hard disk (HD), a flexible disk (FD), or a card memory connected via an adapter to a Personal Computer Memory Card International Association (PCMCIA) card slot, which stores a boot program, browser software, various applications, font data, user files, editing files, and various types of data.

A communication interface controller (communication I/F C) 208 is configured to connect and communicate with, via a network, an external device such as a storage device that stores an image obtained by a medical image diagnostic apparatus such as a CT scanner, and executes a communication control process through the network. For example, the communication I/F controller 208 is capable of performing communication via the Internet using the Transmission Control Protocol and Internet Protocol (TCP/IP).

Note that the CPU 201 is capable of performing display on the display 210 by, for example, developing (rasterizing) an outline font onto a display information region in the RAM 203.

The CPU 201 also enables a user instruction to be given through a mouse cursor (not illustrated) on the display 210.

Various programs and the like used to enable the medical imaging apparatus 101 according to the embodiments of the present invention to execute later-described various processes are recorded in the external memory 211, and these programs are loaded as needed to the RAM 203, thereby enabling the CPU 201 to execute the programs.

Furthermore, definition files and various information tables used by a program according to the embodiments of the present invention are stored in the external memory 211.

First Embodiment

Figure 2:
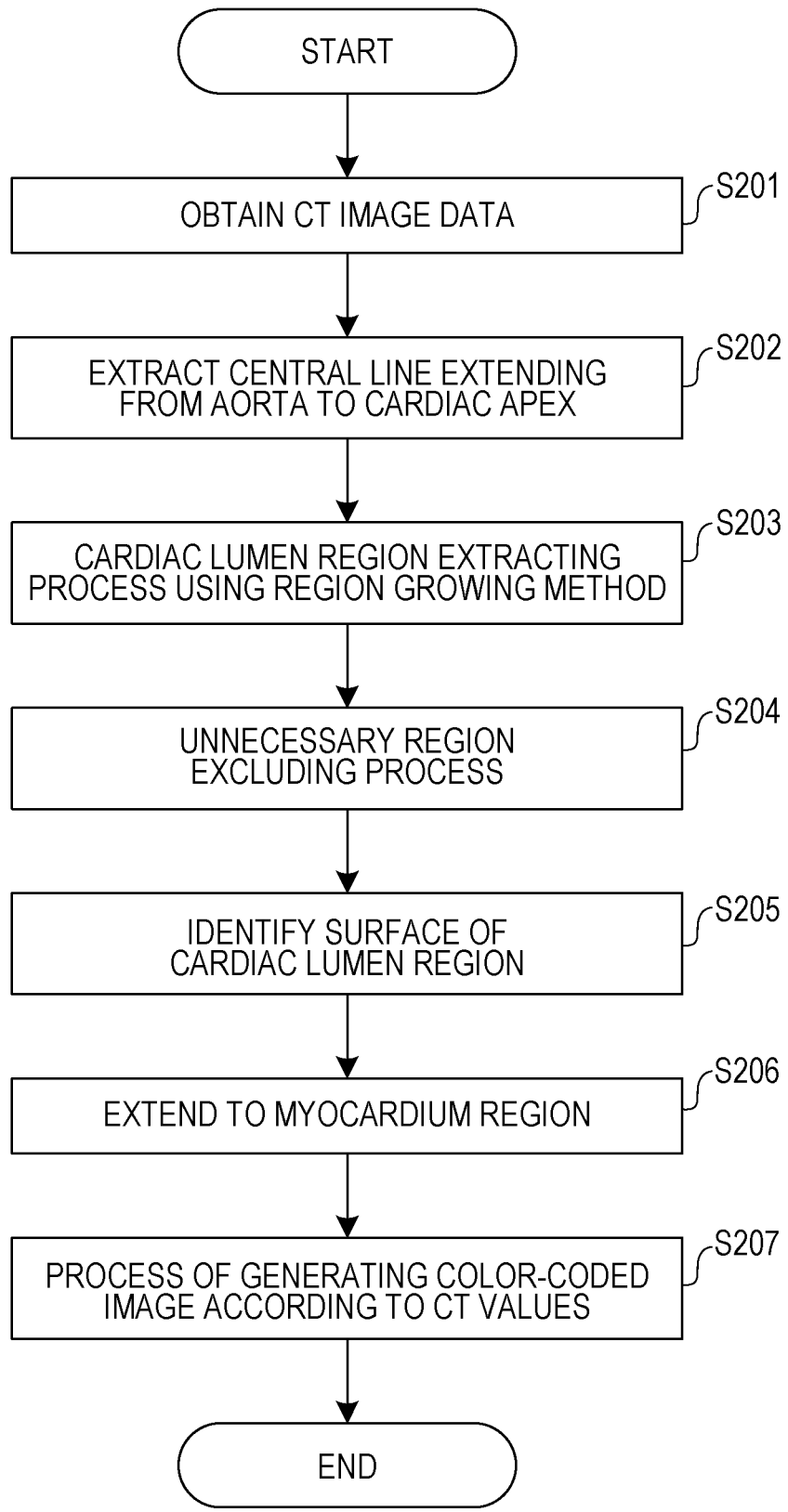
FIG. 2 is a flowchart describing the flow of a medical imaging process according to an embodiment of the present invention.

FIG. 2 is a flowchart describing the flow of a medical imaging process executed by the medical imaging apparatus 101 according to a first embodiment of the present invention. The process illustrated in the flowchart of FIG. 2 is implemented by reading and executing a stored control program by the CPU 201 of the medical imaging apparatus 101.

In S201 of FIG. 2, the CPU 201 of the medical imaging apparatus 101 obtains, from a storage device (not illustrated), coronary vein CT image data obtained by a medical image diagnostic apparatus such as a CT scanner. The coronary vein CT image data obtained here is a plurality of slice images constituting one item of volume data.

Figure 3:
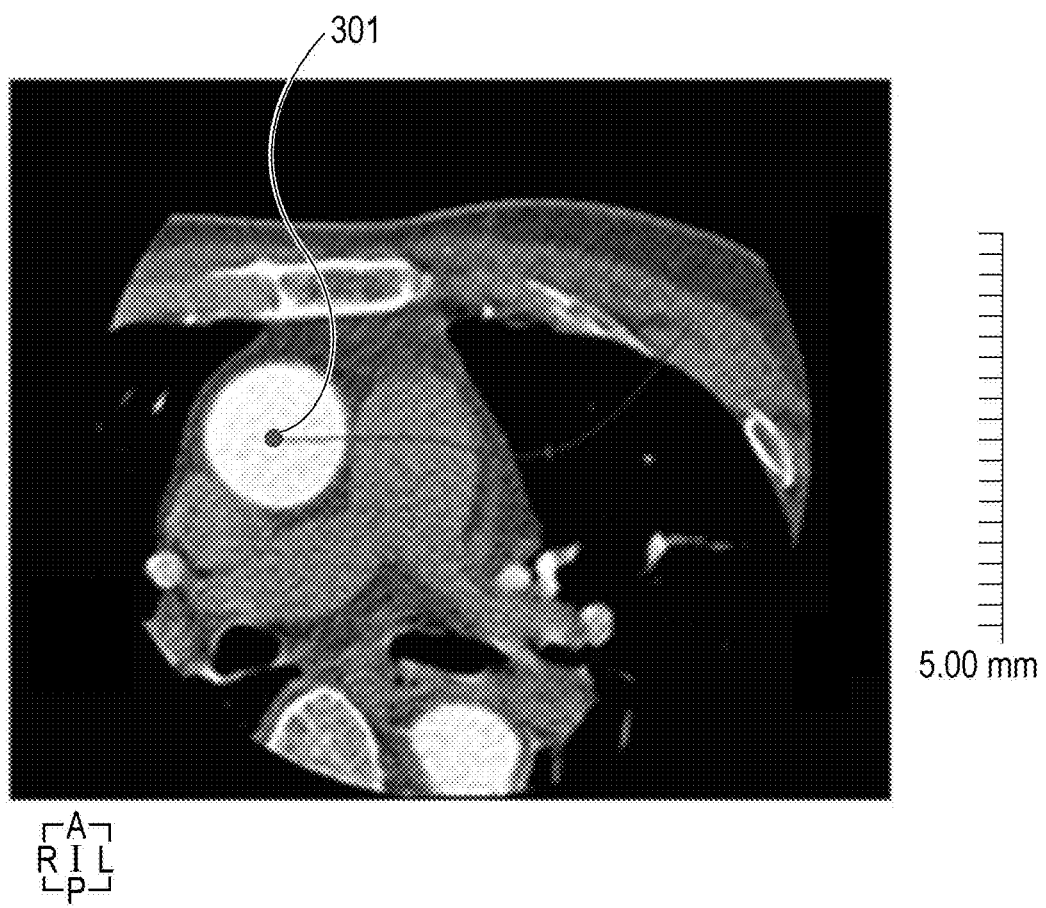
FIG. 3 is a diagram describing how a centroid of the aorta is identified.
Figure 4:
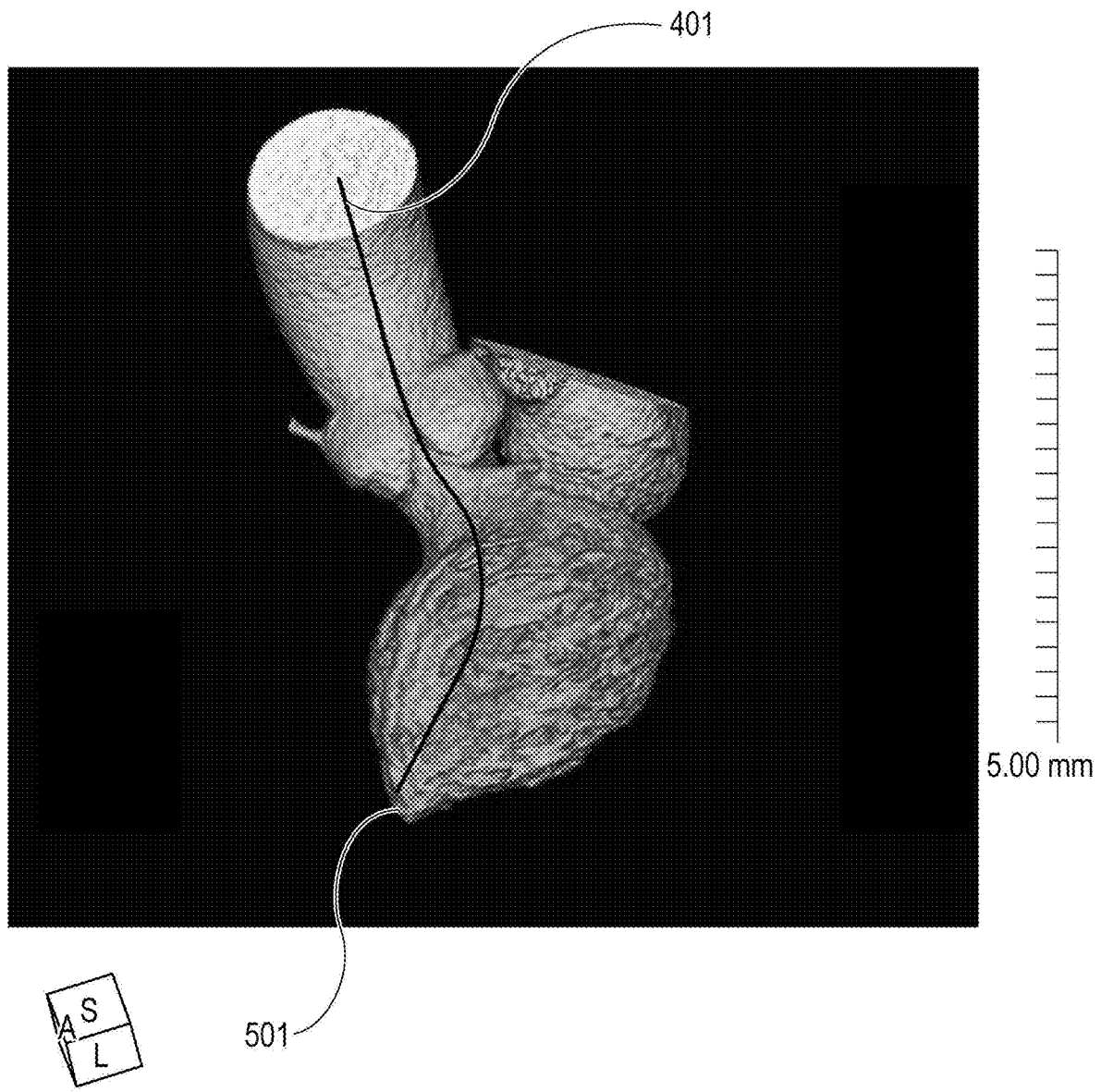
FIG. 4 is a diagram describing a central line generated by connecting the centroid in each image.

In S202, the CPU 201 of the medical imaging apparatus 101 identifies the centroid of a high signal value region (region with high CT values) with a high degree of circularity in a slice image of the aorta side included in the obtained CT image data. FIG. 3 illustrates the position of a centroid 301, identified in a slice image of the aorta side. Furthermore, similar identification operations are sequentially performed, starting from the aorta side, on a plurality of slice images constituting the volume data, until there remains no high signal value region, and the identified centroids are connected to extract a central line. It can be said that a high signal value region with a high degree of circularity is the aorta. By performing identification operations, starting from the aorta side, on slice images, a central line can be certainly identified as a pathway that extends from the aorta to a cardiac apex 501 of the left ventricle, which causes an ischemic disease. FIG. 4 illustrates by way of example a central line 401 connecting the aorta, which is identified by connecting the centroids 301 in the slice images as described above, and the cardiac apex 501 of the left ventricle. Note that the slice images used here include not only slice images captured by a CT scanner, but also slice images that are reconfigured from the volume data. Although the above example discusses the case where the central line is generated by connecting the centroids 301 in the slice images, other methods may be used as long as these methods are capable of extracting portions near the center of high signal value regions.

In S203, the CPU 201 of the medical imaging apparatus 101 performs a cardiac lumen region extracting process (region identification) using a region growing method on the central line 401 extracted in S202, starting from the cardiac apex 501 side. The region glowing method is a technique that can track a signal value on the basis of some sort of index from an arbitrary pixel (extraction start point). Using this technique, tracking is performed on the basis of the central line 401 as an index, starting from the cardiac apex 501 side, thereby extracting a high signal value region based on a radiocontrast agent. In doing so, a cardiac lumen region ranging from the cardiac apex 501 of the left ventricle to the aorta and further toward the mitral valve can be extracted.

FIGS. 5A to 5D illustrate how extraction is performed using the region growing method. FIGS. 5A and 5B illustrate states in which only a cardiac lumen is extracted. FIG. 5C illustrates a state in which, besides the cardiac lumen region, an aorta 502 is started to be extracted. FIG. 5D illustrates a state in which extraction of the cardiac lumen region is almost completed, and extraction of a left ventricle 503 is started.

Extraction of the cardiac lumen region may be stopped at a time at which the cardiac lumen region has been sufficiently extracted. Since the size of the heart varies from one patient to another, the time to stop extraction is preferably determined by taking into consideration changes in the volume of the cardiac lumen region being extracted.

Figure 6:
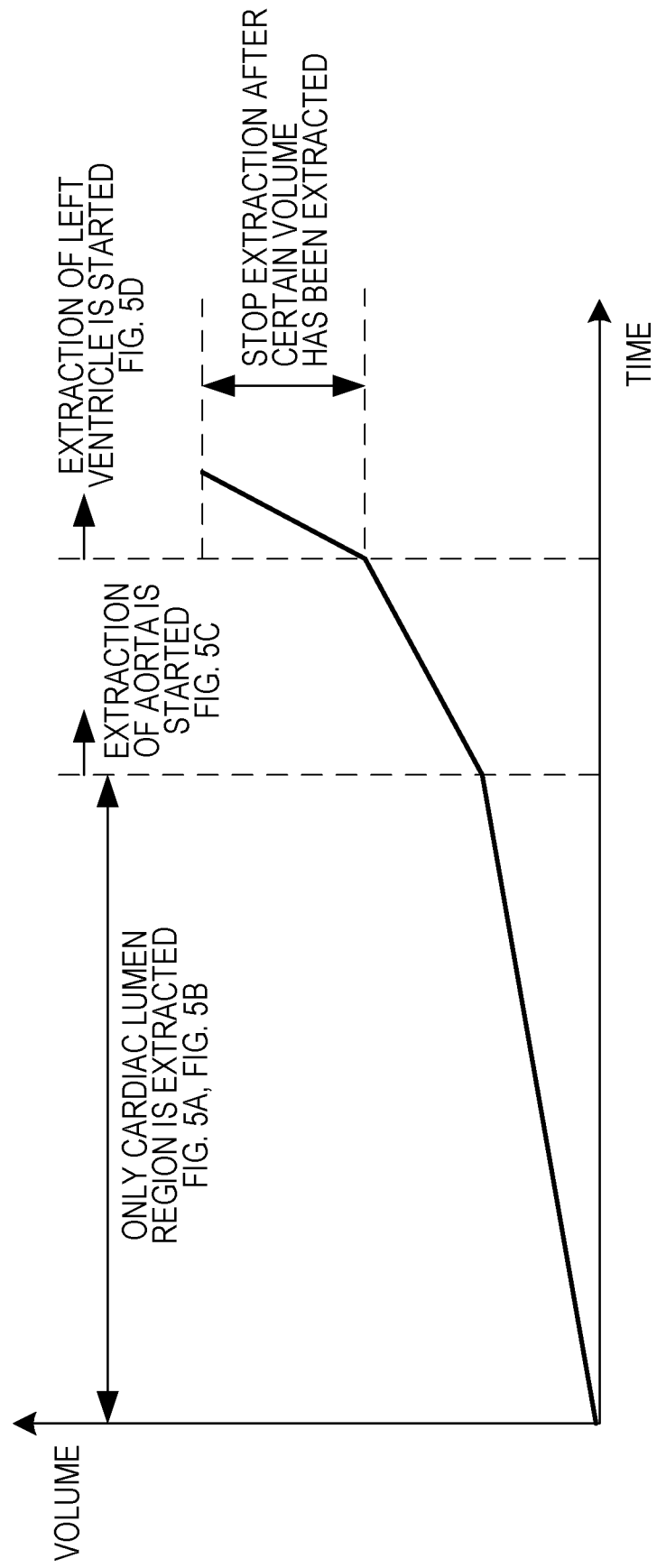
FIG. 6 is a diagram illustrating the relationship between changes in volume of the cardiac lumen region extracted by the region growing method and time.

FIG. 6 is a diagram illustrating the relationship between the course of time and changes in the volume of the extracted cardiac lumen region using the region growing method. As is clear from the diagram, the growth rate of the volume is substantially constant in a period of time in which only the cardiac lumen region is extracted. However, when extraction of the aorta starts, the growth rate of the volume becomes faster than before. Furthermore, when extraction of the left ventricle starts, the growth rate of the volume becomes yet faster. In short, if the extraction process is stopped after the appearance of the second inflection point of the growth rate of the volume, the cardiac lumen region can be certainly extracted from any patient's heart images. Specifically, the extraction process is preferably controlled to be stopped at a time at which a certain amount of volume has been extracted or a certain period of time has elapsed after the appearance of the second inflection point.

Next, in S204, the CPU 201 of the medical imaging apparatus 101 performs a process of excluding an unnecessary region included in the cardiac lumen region extracted in S203. Note that the unnecessary region excluding process is preferably performed to improve the identifiability of an image, though this process is not an essential process.

Figure 8:
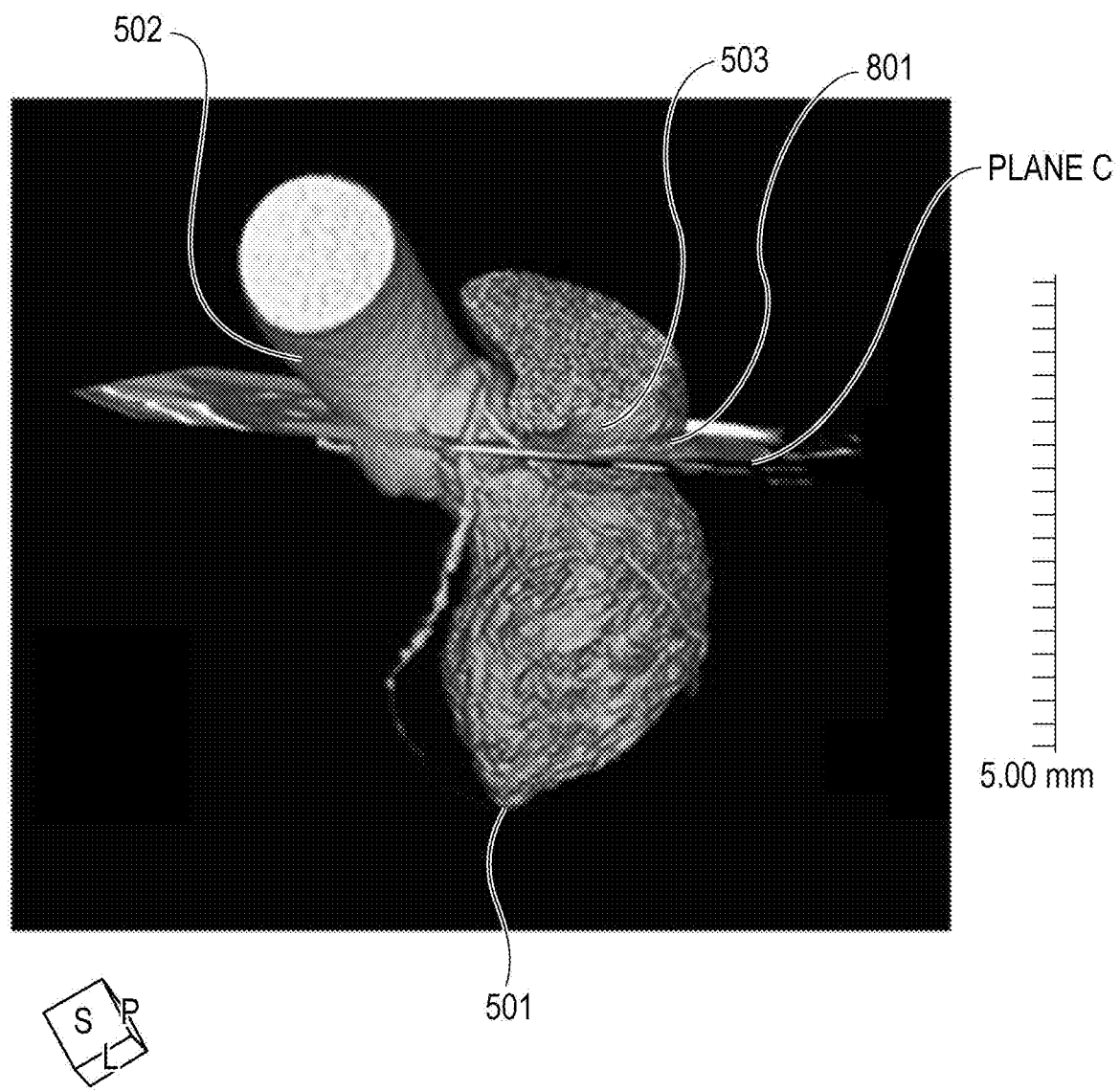
FIG. 8 is a diagram describing a process of excluding an unnecessary region.

As a specific process, as illustrated in FIG. 7A, a plane B connecting two coronary arteries 701 in the image, extracted in S203, is identified. Thereafter, as illustrated in FIG. 7B, a plane B' is identified by translating in parallel the plane B by about 1 cm toward the cardiac apex side. Since a region on the aorta side (upper side) with respect to the plane B' is a region not to be used for diagnosis of ischemia, the region can be excluded. Furthermore, the same applies to a region on the mitral valve side (left ventricle side), and a plane C along with a left circumflex coronary artery 801 identified from the image extracted in S203 is identified (FIG. 8). Since a region above the plane C is a region not to be used for diagnosis of ischemia, the region can be excluded.

Figure 9:
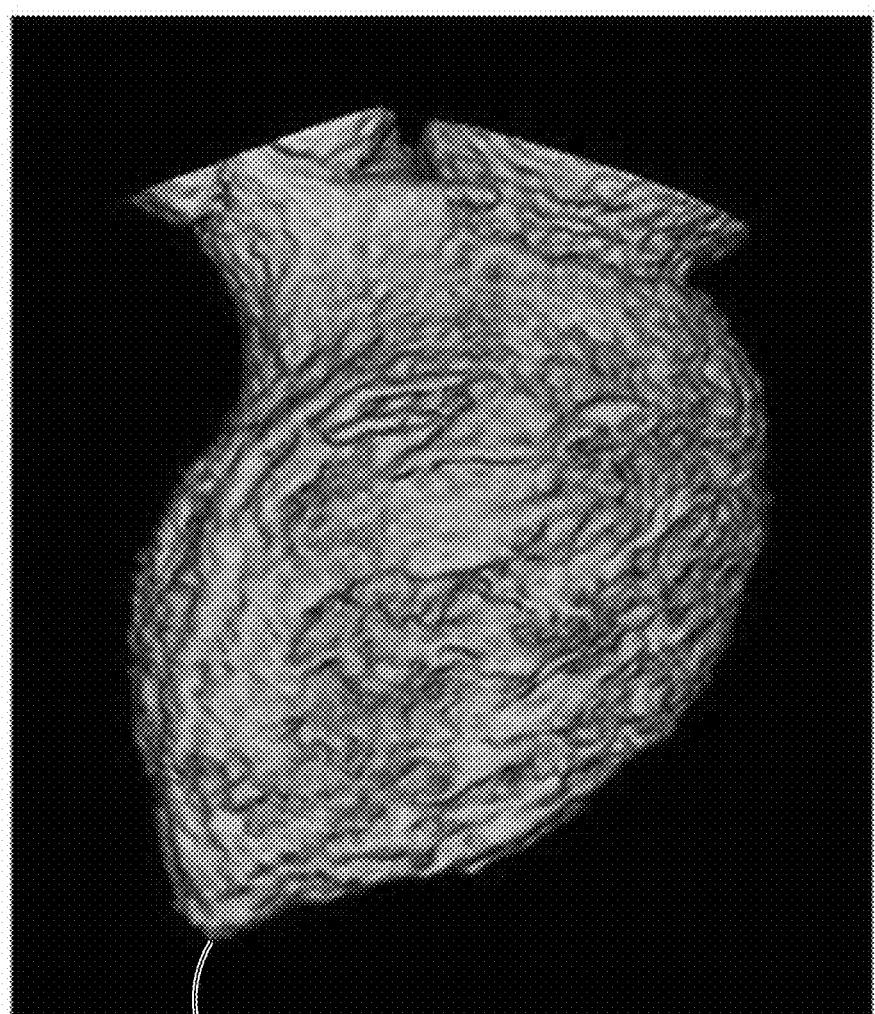
FIG. 9 is a diagram illustrating a cardiac lumen region after unnecessary regions have been excluded.

In this manner, by identifying the plane B' and the plane C and excluding unnecessary regions, a three-dimensional color-coded image including no unnecessary region can be obtained by performing a process of coloring different parts of the myocardium region in different colors. When this image is used by a doctor for diagnosis, whether an ischemic region has been generated can be more easily identified. FIG. 9 illustrates a cardiac lumen region identified by excluding unnecessary regions from the cardiac lumen region extracted in S203.

In S205, the CPU 201 of the medical imaging apparatus 101 identifies a surface 1101 of the cardiac lumen region on the basis of the cardiac lumen region identified (cardiac lumen identification) by excluding unnecessary regions from the cardiac lumen region extracted in S203 in this manner. Although the embodiment has discussed above the exemplary case in which extraction is performed using the region growing method, other methods may be used as long as these methods can extract a cardiac lumen region.

In S206, the CPU 201 of the medical imaging apparatus 101 performs a process of extending the surface 1101 of the cardiac lumen region to a myocardium region including the endocardium. Specifically, the surface position of the cardiac lumen region in each CT image is extended by a few pixels (a certain distance) at a time toward the myocardium side, and a position distant from the surface 1101 of the cardiac lumen region by a certain amount (about 5 mm) is identified as a face 1102 (virtual face) of a myocardium region (myocardium identification). If the distance extended here can be adjusted to an optimal distance, the position becomes appropriate for early diagnosis of an ischemic lesion. Regarding how great the inward distance is from the surface 1101 of the cardiac lumen region, the setting is preferably changeable by the user accordingly. It is not necessary to have the distance extended be equal in all regions, and the distance extended may be changed in accordance with the region in the heart.

Figure 10:
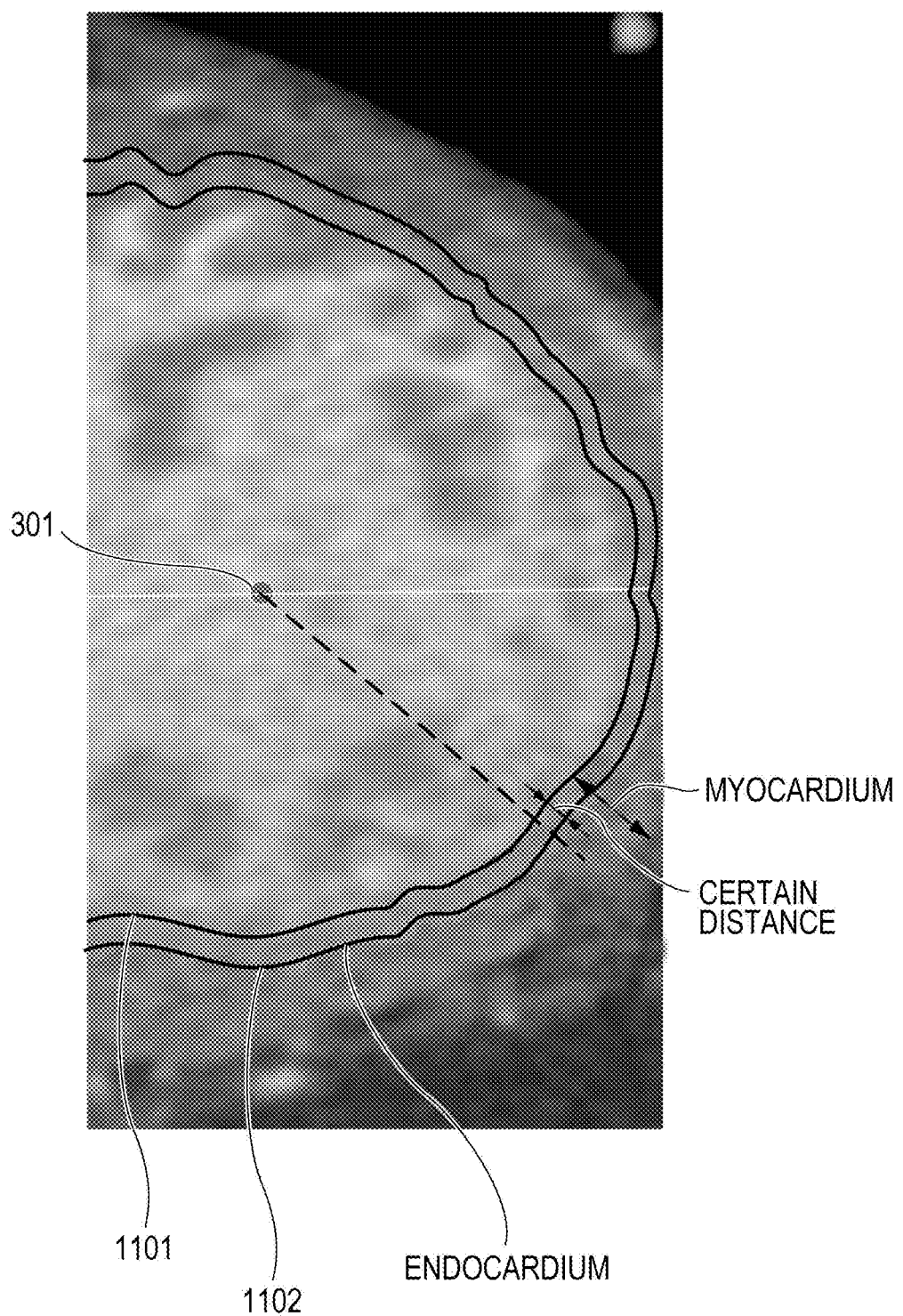
FIG. 10 is a diagram for describing a surface of the cardiac lumen region and a face of a myocardium region.

FIG. 10 illustrates a CT slice image including the surface 1101 of the cardiac lumen region, identified in S205, and the face 1102 of the myocardium region. As is clear from the image, each point of the surface 1101 of the cardiac lumen region is displaced by a certain distance at a time along a straight line connecting the centroids 301, thereby identifying the face 1102 of the myocardium region.

In S207, the CPU 201 of the medical imaging apparatus 101 performs a process of generating a three-dimensional image in which the face 1102 of the myocardium region, identified in S206, is colored in accordance with the level of a CT value according to each coordinate position included in the face 1102. A color-coded image generated thereafter is saved in the external memory 211 of the medical imaging apparatus 101, for example, and is displayed on the display 210 or the like, thereby enabling the user such as a doctor to visually recognize the image.

Figure 11:
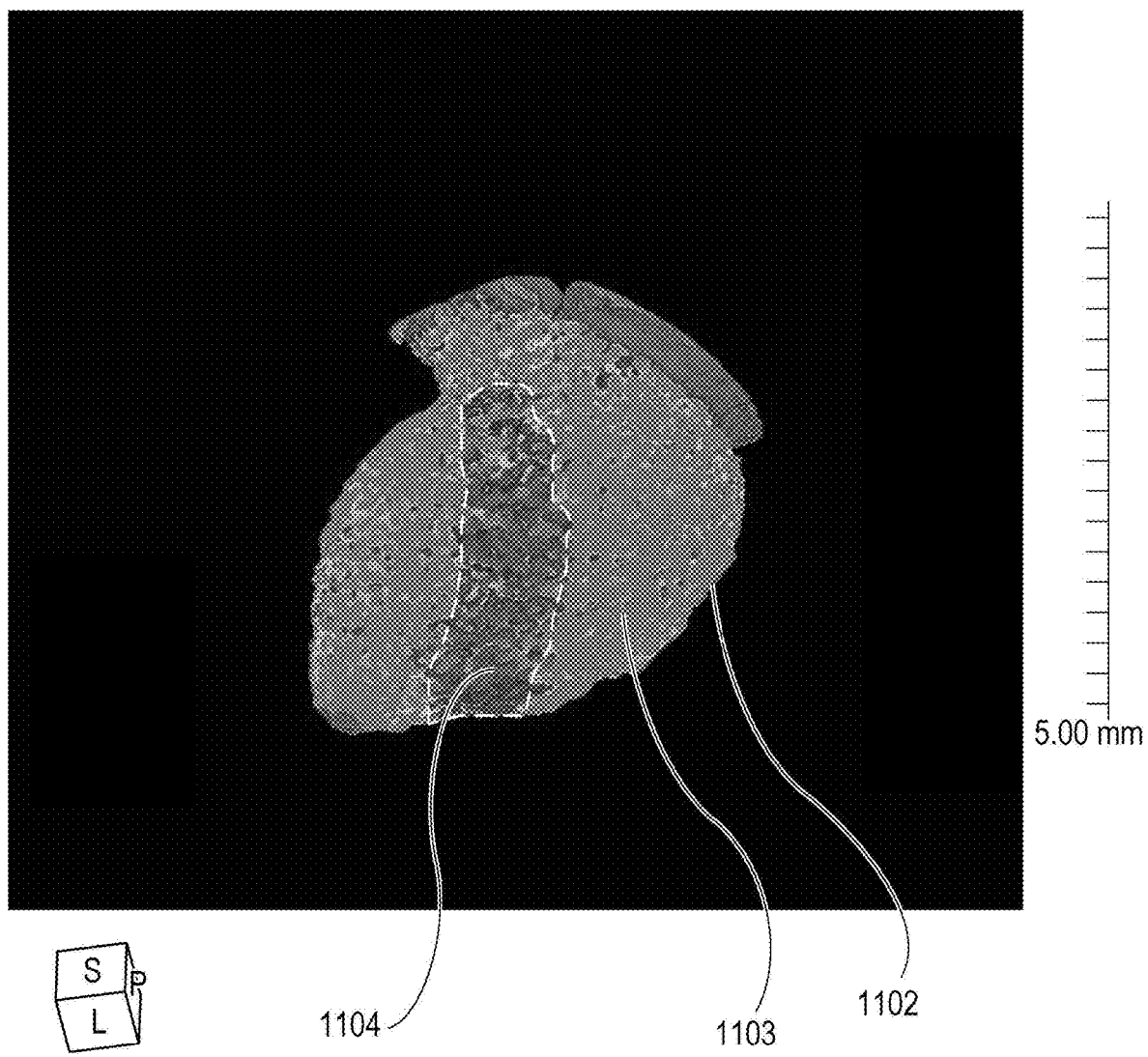
FIG. 11 is a color-coded image of the face of the myocardium region.

The color coding method may have, for example, 100 as a preset threshold. A CT value greater than or equal to 100 is colored in red, and a CT value less than 100 is colored in blue. Alternatively, stepwise thresholds are set, and the following color-coded image may be generated. That is, a CT value greater than or equal to 110 is colored in red; a CT value less than 110 and greater than or equal to 100 is colored in orange; a CT value less than 100 and greater than or equal to 90 is colored in green; a CT value less than 90 and greater than or equal to 80 is colored in blue; and a CT value less than 80 is colored in black. Furthermore, a color-coded image may be generated not only by setting a threshold(s), but also a color-coded image may be generated using gradations of color. FIG. 11 illustrates an example of an image generated by performing such a color coding process on the face 1102 of the myocardium region. Here, a region 1103 with CT values that are greater than or equal to 100, which is likely to be in a normal state, and a region 1104 with CT values that are less than 100, which is likely to be in an ischemic state, are displayed in an identifiable manner. That is, differences in the signal level on the surface 1102 of the myocardium region are displayed in different colors, making it easy to identify the state of the heart. Note that color coding according to the embodiment includes coloring of different parts in different color tones by adjusting brightness or contrast.

Figure 12:
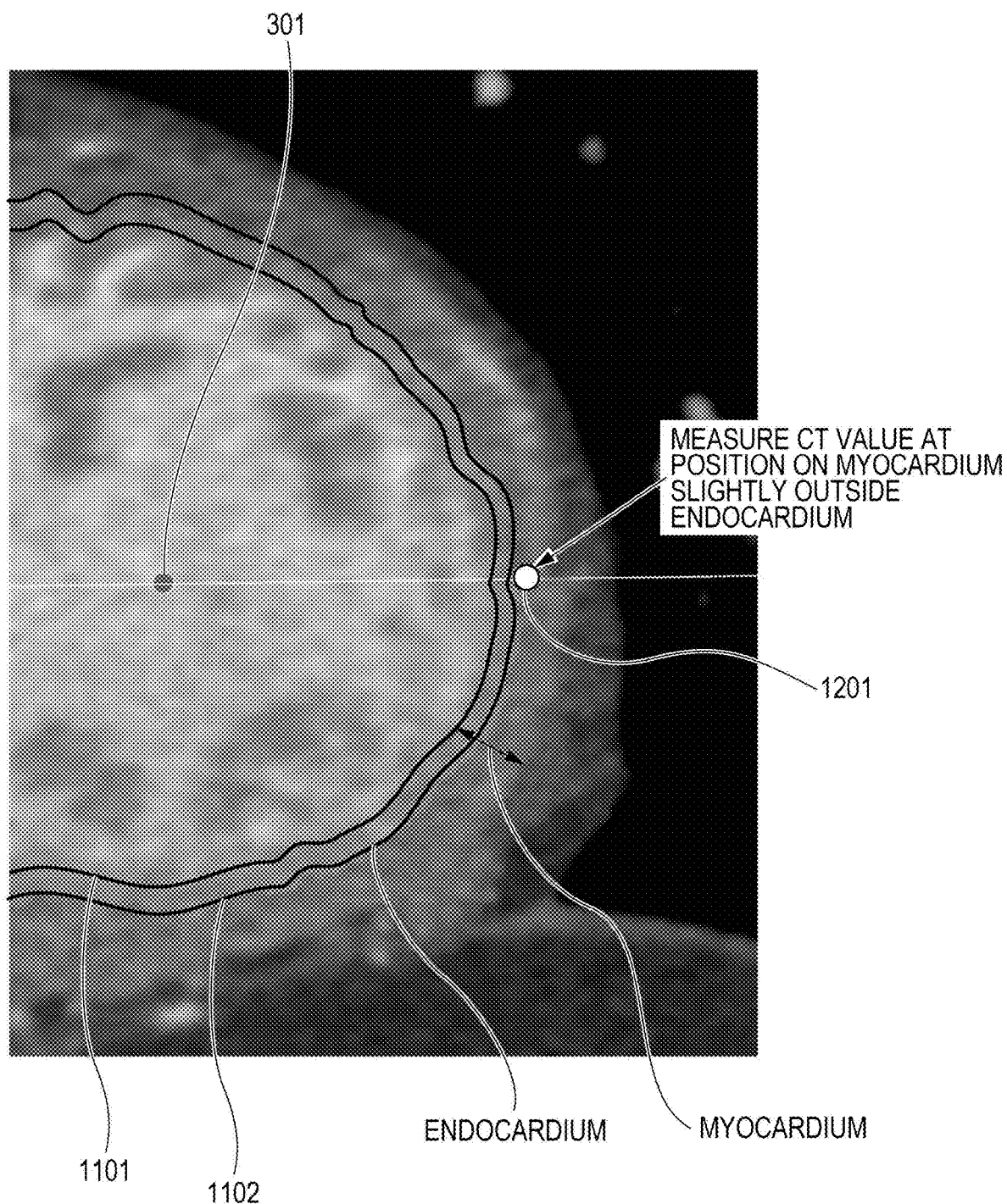
FIG. 12 is a diagram describing a position for obtaining a threshold.
Figure 13:
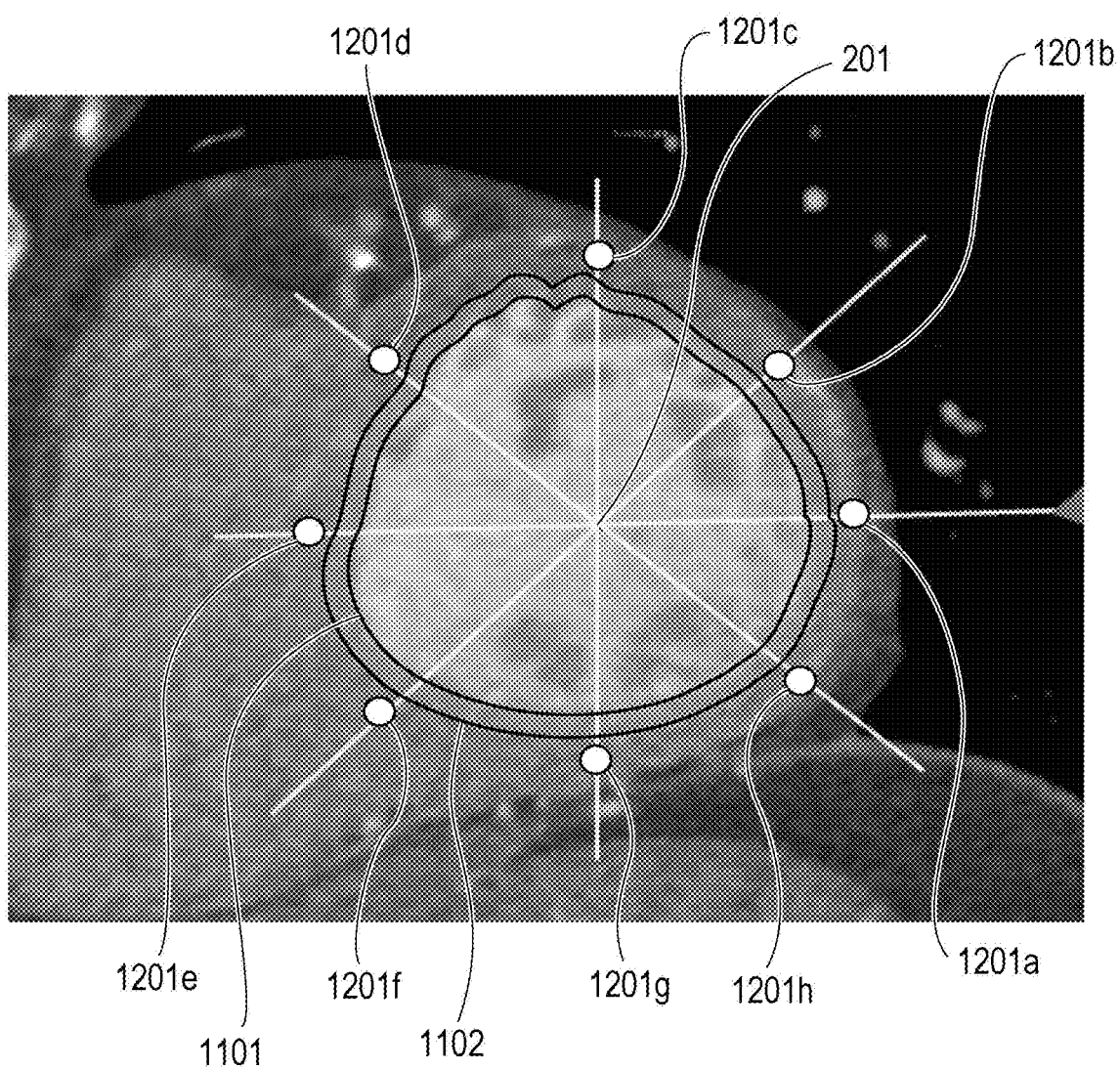
FIG. 13 is a diagram describing positions for obtaining a threshold.

By defining a preset threshold on the basis of a value obtained in a normal myocardium region, it is highly likely that an image substantially suitable for determining narrowing of the coronary arteries can be obtained. Therefore, a CT value at a position 1201 that is exterior of the face 1102 of the myocardium region in one slice image and that is within the range of the myocardium may be set as an initial threshold value, as illustrated in FIG. 12, and a process of generating a color-coded image may be performed on the basis of the set threshold. Furthermore, as illustrated in FIG. 13, CT values at a plurality of positions (1201a to 1201h) that are exterior of the face 1102 of the myocardium region and that are within the range of the myocardium may be obtained, an average of these CT values may be set as an initial threshold value, and a process of generating a color-coded image may be performed on the basis of the set threshold. In the case of obtaining CT values at a plurality of positions, in order to average the variations, CT values are preferably obtained at positions equidistant from the centroid 301 of one slice image. Furthermore, CT values obtained not only from one slice image, but also from a plurality of slice images may be used.

Adjusting such a threshold to an optimal value can contribute to color coding for early diagnosis of an ischemic lesion. A preset threshold (initial value) is preferably made adjustable by the user appropriately by operating a tool bar or the like.

As described above, a face of a myocardium region is identified on the basis of a cardiac lumen region, and on that face a color-coded image based on which the state of the left ventricular endocardium that sensitively reacts to myocardial ischemia can be identified is generated, thereby providing an image that can contribute to reducing oversight of ischemic lesions. Furthermore, unlike a technique of the related art, it is unnecessary to obtain a plurality of items of volume data, and a three-dimensional color-coded image is generated from a medical image including a heart region that is one item of volume data, thereby reducing the amount of image data to be captured, and providing an image for diagnosis of narrowing of coronary arteries while reducing the patient's exposure to radiation.

Second Embodiment

Although the first embodiment has discussed the exemplary case in which a color-coded image based on which the state of the left ventricular endocardium can be identified is generated and displayed, not only the left ventricular endocardium, but also the coronary arteries and the like may be additionally displayed together. A second embodiment will discuss the exemplary case in which, besides the left ventricular endocardium, the coronary arteries are superimposed and displayed. In the second embodiment, points that are different from the first embodiment will be mainly described, and descriptions of points that are the same as the first embodiment will be omitted.

Figure 14:
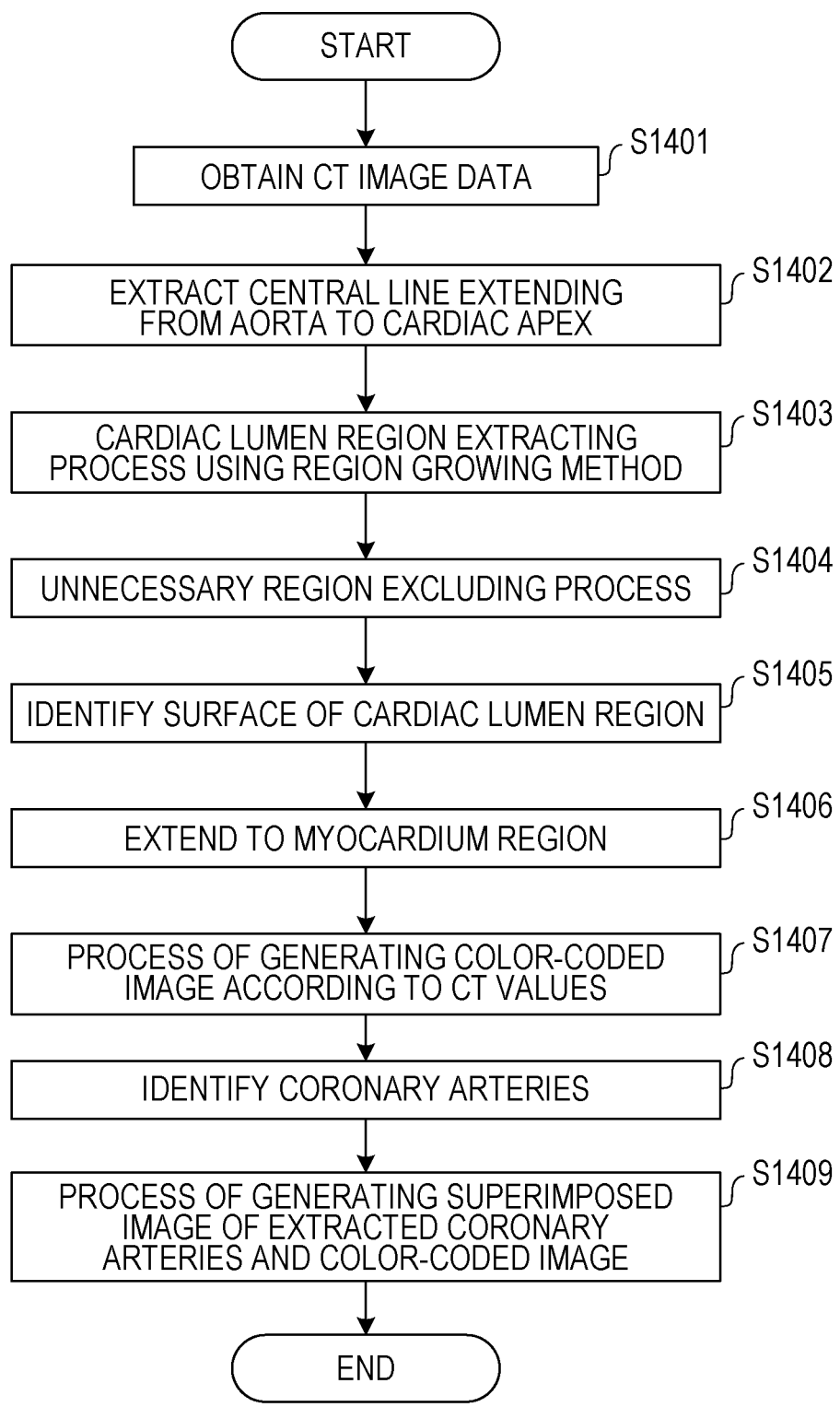
FIG. 14 is a flowchart describing the flow of a medical imaging process according to an embodiment of the present invention.

FIG. 14 is a flowchart describing the flow of a medical imaging process executed by the medical imaging apparatus 101 according to the second embodiment. The process illustrated in the flowchart of FIG. 14 is implemented by reading and executing a stored control program by the CPU 201 of the medical imaging apparatus 101.

Since the processing in S1401 to S1407 of FIG. 14 is the same as the processing in S201 to S207 of FIG. 2, a description thereof will be omitted.

Figure 15A:
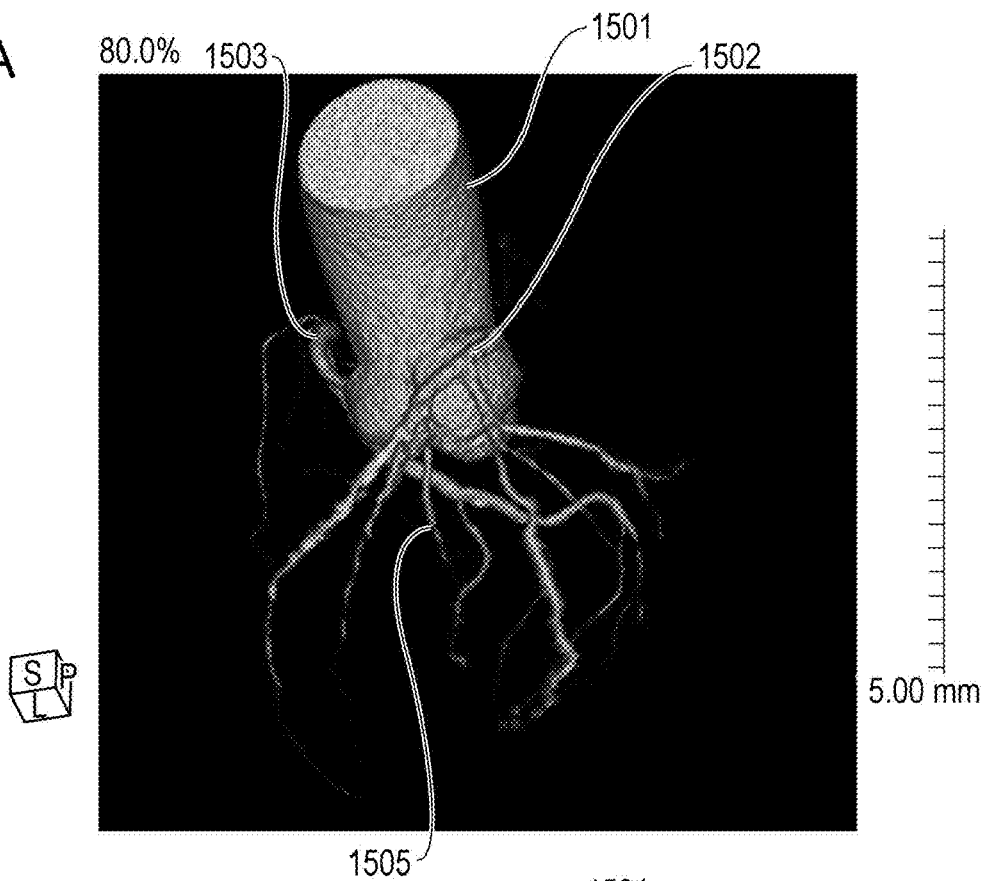
FIG. 15A is an image of extracted coronary arteries and the like, and FIG. 15B is an image obtained by combining the image of extracted coronary arteries and the like with a color-coded image of a virtual face.

In S1408, the CPU 201 of the medical imaging apparatus 101 identifies, from the CT image obtained in S1401, coronary arteries for supplying oxygen to the myocardium (coronary artery identifying unit). FIG. 15A illustrates exemplary blood vessels such as coronary arteries identified as above. Here, a left coronary artery 1502 and a right coronary artery 1503 branching off from an aorta 1501 are identified. Since such coronary arteries branch off from the root of the aorta, such coronary arteries can be identified by extracting blood vessels that branch off. Note that this process of identifying coronary arteries may be performed in advance before a color-coded image is generated.

In S1409, the CPU 201 of the medical imaging apparatus 101 generates a superimposed image by superimposing the coronary arteries identified in S1408 on a color-coded image generated according to CT values in S1407. Regarding the aorta side, it is preferable to identify portions near the position of the plane B' and the plane C identified in the process of excluding unnecessary regions in S1404, and to consecutively display the coronary arteries, the aorta, and the color-coded image. Thereafter, the superimposed image is saved in the external memory 211 of the medical imaging apparatus 101, for example, and is displayed on the display 210 or the like, thereby enabling the user such as a doctor to visually recognize the image.

Figure 15B:
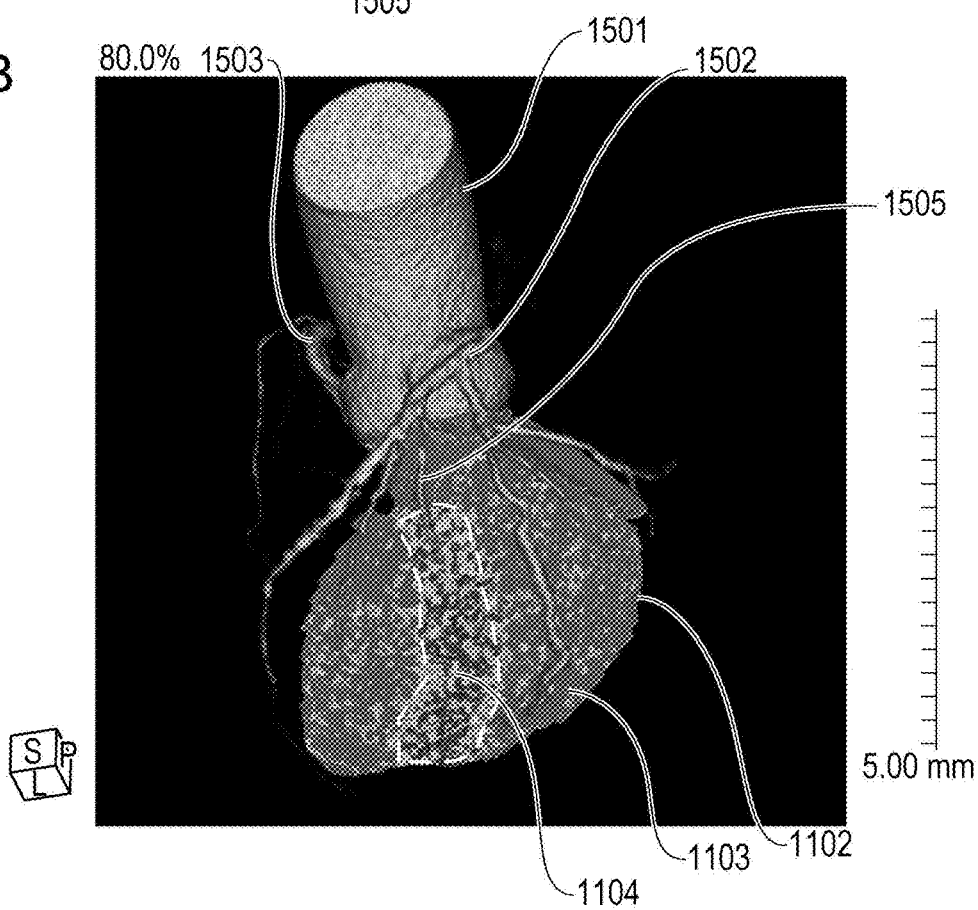

FIG. 15B illustrates an example of an image obtained by combining images in S1409. By displaying the coronary arteries and the color-coded image together as described above, which blood vessel is a coronary artery for delivering blood to the region 1104 with CT values that are less than 100, which is likely to be in an ischemic state, can be easily identified. That is, a blood vessel that is highly likely to have a narrowing can be easily identified. In the example illustrated in FIG. 15B, it is clear that a first diagonal branch 1505 is positioned near the region 1104 which is highly likely to be in an ischemic state. Thus, the point that it is highly possible that there is a narrowing in the first diagonal branch 1505 can be easily identified.

Figure 16:
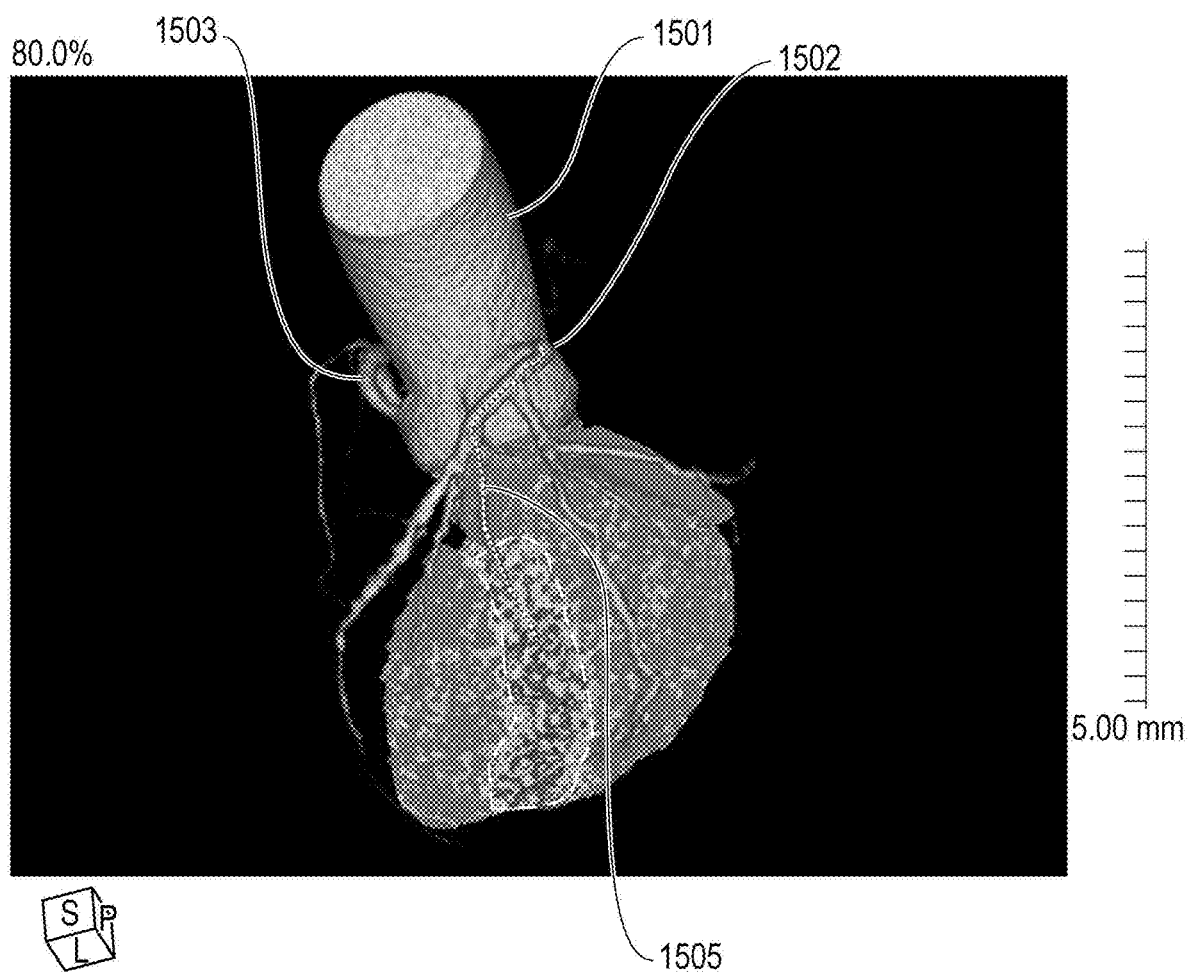
FIG. 16 is an image obtained by combining the image of extracted coronary arteries and the like with a color-coded image of a virtual face.

Alternatively, a portion of the face of the myocardium region that has CT values less than a preset threshold may be identified as the region 1104 which is highly likely to be in an ischemic state, and further a blood vessel superimposed on the region 1104 (or a blood vessel near the region 1104) may be identified. As illustrated in FIG. 16, the pathway of the blood vessel may be emphasized by a broken line, for example, and displayed. Accordingly, the user such as a doctor can easily identify the blood vessel which is highly likely to have a narrowing. By defining a preset threshold on the basis of a value obtained in a normal myocardium region, as has been described in the first embodiment, it is highly likely that a region substantially suitable for determining narrowing of the coronary arteries can be identified.

Although the embodiments have discussed above the example of using, as a medical image, a CT image captured by a CT scanner in systole of a patient into which a radiocontrast agent has been injected, a magnetic resonance angiographic (MRA) image captured by a magnetic resonance (MR) scanner in systole may also be used.

The embodiments of the present invention include embodiments as, for example, a system, an apparatus, a method, a program, or a storage medium. Specifically, the embodiments of the present invention may be applied to a system including a plurality of devices, or may be applied to an apparatus including only one device. Note that the embodiments of the present invention include a software program implementing the functions of the above-described embodiments, which is directly supplied to a system or an apparatus, or which is supplied from a remote place. The embodiments of the present invention also include the system or the apparatus which reads and executes the supplied program code to implement the functions.

Therefore, program code itself to be supplied to and installed in an information processing apparatus in order to implement, on the information processing apparatus, the functions and processes according to the above-described embodiments also implements the present invention. In other words, a computer program itself for implementing the above-mentioned functions and processes is also included in the embodiments of the present invention.

In that case, such a program may have any form such as object code, a program executed by an interpreter, or script data supplied to an OS, as far as it functions as a program.

Examples of recording media for supplying a program include a flexible disk, a hard disk, an optical disk, a magneto-optical disk (MO), a compact-disc read-only memory (CD-ROM), a compact-disc recordable (CD-R), and a compact-disc rewritable (CD-RW). Other examples include a magnetic tape, a non-volatile memory card, a ROM, and a digital versatile disc (DVD including DVD-ROM and DVD-R).

Moreover, one method of supplying a program includes connecting to a homepage on the Internet by using a browser on a client computer. A computer program according to the embodiments of the present invention can be supplied by downloading the computer program itself from the homepage or by downloading a file including the compressed computer program with an auto-install function to a recording medium such as a hard disk.

Program code configuring a program according to the embodiments of the present invention can be divided into a plurality of files, and these files can be downloaded from different homepages, thereby implementing the above-described functions and processes. In other words, a World Wide Web (WWW) server that enables a plurality of users to download a program file for implementing, with an information processing apparatus, the functions and processes according to the embodiments of the present invention is also included in the embodiments of the present invention.

A program according to the embodiments of the present invention may be encrypted, stored on a storage medium such as a CD-ROM, and distributed to a user. A user who satisfies a certain condition may be allowed to download key information for decrypting the encryption from a homepage via the Internet. Using the downloaded key information, the user may decrypt the encrypted program and install the decrypted program in an information processing apparatus, thereby implementing the functions and processes.

Alternatively, the functions of the above-described embodiments are implemented by an information processing apparatus that executes a program that has been read. Moreover, on the basis of an instruction of the program, an OS running on the information processing apparatus, for example, may perform the entirety or part of the actual processing, and that processing may implement the functions of the above-described embodiments.

Furthermore, a program read out from a recording medium is written on a memory included in a feature expansion board inserted in an information processing apparatus or a feature expansion unit connected to an information processing apparatus. Thereafter, on the basis of an instruction of the program, a CPU included in the feature expansion board or the feature expansion unit performs the entirety or part of the actual processing, and that processing implements the functions of the above-described embodiments.

Note that the above-described embodiments are merely examples of the embodiments of the present invention, and the technical scope of the present invention is not construed to be restrictively interpreted by these embodiments. That is, the present invention can be implemented in various forms without departing from the technical spirit or major features of the present invention.

According to the above-described embodiments, an image provided for diagnosis of narrowing of coronary arteries can be generated by using a medical image captured in systole. By identifying a face of a myocardium region using a cardiac lumen region and displaying that face in colors according to signal values of a medical image at positions on the face, an image provided for diagnosis of narrowing of coronary arteries can be provided by using only a medical image including a heart region that is one item of volume data.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-209259, filed Oct. 10, 2014, and Japanese Patent Application No. 2015-131597, filed Jun. 30, 2015, which are hereby incorporated by reference herein in their entirety.

What is claimed is:

1. A medical image processing apparatus comprising:
a first identifying unit configured to identify a face of a myocardium region, using a three-dimensional medical image including a heart region;
a first generation unit configured to generate a three-dimensional color-coded image colored according to signal values on the identified face of the myocardium region;
a second identifying unit configured to identify a coronary artery, using the three-dimensional medical image;
a second generation unit configured to generate a three-dimensional image of the coronary artery along a line of a sight of the three-dimensional color-coded image of the myocardium region, based on the coronary artery identified by the second identifying unit; and
a display control unit configured to cause a display unit to display a superimposed image generated by superimposing the three-dimensional image of the coronary artery on the three-dimensional color-coded image of the myocardium region.

2. The medical image processing apparatus according to claim 1, further comprising:
a third identifying unit configured to identify, out of the face of the myocardium region, a region with a signal value that is less than a certain threshold;
wherein the display control unit causes the display unit to display the superimposed image such that a blood vessel superimposed on the identified region or a blood vessel near the identified region becomes identifiable.

3. The medical image processing apparatus according to claim 1,
wherein the first generation unit generates the three-dimensional color-coded image based on which a level difference is identifiable, by coloring the image in different colors on a basis of a threshold.

4. The medical image processing apparatus according to claim 3,
wherein the threshold is set stepwise.

5. The medical image processing apparatus according to claim 3,
wherein the threshold is determined using a signal value obtained in a normal myocardium region.

6. The medical image processing apparatus according to claim 1, wherein the first identifying unit identifies the face of the myocardium region toward a cardiac lumen region.

7. The medical image processing apparatus according to claim 1,
wherein the signal value is a computed tomographic (CT) value.

8. The medical image processing apparatus according to claim 1,
wherein the three-dimensional medical image is volume data captured in systole.

9. The medical image processing apparatus according to claim 1,
wherein the three-dimensional medical image is a computed tomographic (CT) image or a magnetic resonance angiographic (MRA) image.

10. A medical image processing method comprising:
first identification of identifying a face of a myocardium region, using a three-dimensional medical image including a heart region;
first generation of generating a three-dimensional color-coded image colored according to signal values on the identified face of the myocardium region;
second identification of identifying a coronary artery, using the three-dimensional medical image;
second generation of generating a three-dimensional image of the coronary artery along a line of a sight of the three-dimensional color-coded image of the myocardium region, based on the coronary artery identified by the second identification; and
display control of causing a display unit to display a superimposed image generated by superimposing the three-dimensional image of the coronary artery on the three-dimensional color-coded image of the myocardium region.

11. A medical image processing system comprising:
a medical image processing apparatus including
a first identifying unit configured to identify a face of a myocardium region, using a three-dimensional medical image including a heart region;
a first generation unit configured to generate a three-dimensional color-coded image colored according to signal values on the identified face of the myocardium region;
a second identifying unit configured to identify a coronary artery, using the three-dimensional medical image;
a second generation unit configured to generate a three-dimensional image of the coronary artery along a line of a sight of the three-dimensional color-coded image of the myocardium region, based on the coronary artery identified by the second identifying unit; and
a display control unit configured to cause a display unit to display a superimposed image generated by superimposing the three-dimensional image of the coronary artery on the three-dimensional color-coded image of the myocardium region.

12. A non-transitory computer-readable recording medium having stored thereon a program for causing a computer to perform a medical imaging method comprising:
first identification of identifying a face of a myocardium region, using a three-dimensional medical image including a heart region;
first generation of generating a three-dimensional color-coded image colored according to signal values on the identified face of the myocardium region;
second identification of identifying a coronary artery, using the three-dimensional medical image;
second generation of generating a three-dimensional image of the coronary artery along a line of a sight of the three-dimensional color-coded image of the myocardium region, based on the coronary artery identified by the second identification; and
display control of causing a display unit to display a superimposed image generated by superimposing the three-dimensional image of the coronary artery on the three-dimensional color-coded image of the myocardium region.

* * * * *